US010793792B2

(12) United States Patent
Ding et al.

(10) Patent No.: US 10,793,792 B2
(45) Date of Patent: Oct. 6, 2020

(54) SYSTEMS AND METHODS FOR THE CONVERSION OF HEAVY OILS TO PETROCHEMICAL PRODUCTS

(71) Applicant: Saudi Arabian Oil Company, Dhahran (SA)

(72) Inventors: Lianhui Ding, Dhahran (SA); Essam Al-Sayed, Al-Khobar (SA); Sherif Mohamed, Dhahran (SA); Ibrahim Al-Nutaifi, Dhahran (SA); Alberto Lozano Ballesteros, Dhahran (SA); Ibrahim Abba, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 26 days.

(21) Appl. No.: 15/799,338

(22) Filed: Oct. 31, 2017

(65) Prior Publication Data

US 2018/0327677 A1     Nov. 15, 2018

Related U.S. Application Data

(60) Provisional application No. 62/506,310, filed on May 15, 2017.

(51) Int. Cl.
| | |
|---|---|
| *C10G 69/06* | (2006.01) |
| *C07C 4/04* | (2006.01) |
| *C07C 4/06* | (2006.01) |
| *C07C 7/148* | (2006.01) |
| *C10G 69/14* | (2006.01) |
| *C10G 65/12* | (2006.01) |
| *C10G 69/00* | (2006.01) |

(52) U.S. Cl.
CPC .............. *C10G 69/06* (2013.01); *C07C 4/04* (2013.01); *C07C 4/06* (2013.01); *C07C 7/14808* (2013.01);
(Continued)

(58) Field of Classification Search
CPC ........ C10G 69/00; C10G 69/02; C10G 69/04; C10G 69/06; C10G 57/00; C10G 57/04
(Continued)

(56) References Cited

U.S. PATENT DOCUMENTS 3,617,501 A * 11/1971   Eng .................... C10G 47/00
                                                             208/89
5,000,839 A     3/1991   Kirker et al.
(Continued)

FOREIGN PATENT DOCUMENTS

| FR | 2 367 879 A1 | 4/1978 |
| WO | 2013112965 A1 | 8/2013 |
| WO | 2015/128037 A1 | 9/2015 |

OTHER PUBLICATIONS

International Search Report and Written Opinion dated Jul. 5, 2018, pertaining to International Application No. PCT/US2018/030434, filed May 1, 2018, 14 pages.
(Continued)

*Primary Examiner* — Thuan D Dang
(74) *Attorney, Agent, or Firm* — Dinsmore and Shohl, LLP

(57) ABSTRACT

According to one or more embodiments presently described, a feedstock oil may be processed by a method which may include hydrotreating the feedstock oil to reduce or remove one or more of sulfur content, metals content, nitrogen content, or aromatics content to produce a hydrotreated oil stream; separating at least a portion of the hydrotreated oil stream into a at least a lesser boiling point oil fraction stream and a greater boiling point oil fraction stream in a first separator; hydrocracking the greater boiling point oil fraction stream; and steam cracking the lesser boiling point oil fraction stream.

19 Claims, 2 Drawing Sheets

(52) U.S. Cl.
CPC ............. *C10G 65/12* (2013.01); *C10G 69/00* (2013.01); *C10G 69/14* (2013.01); *C10G 2300/202* (2013.01); *C10G 2300/205* (2013.01); *C10G 2400/02* (2013.01); *C10G 2400/22* (2013.01)

(58) Field of Classification Search
USPC .......... 208/78, 80, 49, 208 R, 251 R, 254 R; 585/652
See application file for complete search history.

(56) References Cited

U.S. PATENT DOCUMENTS

| | | |
|---|---|---|
| 6,576,119 B2 | 6/2003 | Ishida et al. |
| 7,651,604 B2 | 1/2010 | Ancheyta Jurez et al. |
| 7,713,407 B2 | 5/2010 | Tracy, III et al. |
| 7,799,208 B2 | 9/2010 | Kokayeff et al. |
| 9,228,139 B2 | 1/2016 | Shafi et al. |
| 9,228,140 B2 | 1/2016 | Abba et al. |
| 9,255,230 B2 | 2/2016 | Shafi et al. |
| 2007/0090018 A1 | 4/2007 | Keusenkothen et al. |
| 2011/0083996 A1* | 4/2011 | Shafi ...................... C10G 69/06 208/50 |
| 2013/0197285 A1* | 8/2013 | Shafi ...................... C10G 69/06 585/251 |

OTHER PUBLICATIONS

Examination Report pertaining to GCC Application No. 2018-35291 dated May 25, 2020, 6 pgs.
GCC Application No. 2017-333887 filed Nov. 5, 2017, 34 pgs.

\* cited by examiner

SYSTEMS AND METHODS FOR THE CONVERSION OF HEAVY OILS TO PETROCHEMICAL PRODUCTS

CROSS-REFERENCE TO RELATED APPLICATIONS

This application claims priority to U.S. Provisional Patent Application No. 62/506,310 filed May 15, 2017, which is incorporated by reference herein in its entirety.

BACKGROUND

Field

The present disclosure relates to the production of petrochemical products and, more particularly, to systems and method for the direct production of petrochemical products from heavy oils such as crude oil.

Technical Background

Ethylene, propylene, butenes, butadiene, and aromatic compounds such as benzene, toluene, and xylene are basic intermediates for a large portion of the petrochemical industry. They are mainly obtained through the thermal cracking (sometimes referred to as "steam pyrolysis" or "steam cracking") of petroleum gases and distillates such as naphtha, kerosene, or even gas oil. These intermediate compounds may also be produced through refinery fluidized catalytic cracking (FCC) processes, where heavy feedstocks such as gas oils or residues are converted. For example, an important source for propylene production is refinery propylene from FCC units. However, the distillate feedstocks such as gas oils or residues are usually limited and result from several costly and energy intensive processing steps within a refinery.

However, as demands rise for these basic intermediate compounds, other production sources must be considered beyond traditional thermal cracking processes utilizing petroleum gases and distillates as feedstocks.

BRIEF SUMMARY

Accordingly, in view of the ever growing demand of these intermediary petrochemical products such as butene, there is a need for processes to produce these intermediate compounds from other types of feedstocks that are available in large quantities at relatively low cost. The present disclosure is related to processes and systems for producing these intermediate compounds, sometimes referred to in this disclosure as "system products," by the direct conversion of heavy oils such as feedstock crude oil. For example, conversion from a crude oil feedstock may be beneficial as compared with other feedstocks in producing these intermediate compounds because it may be generally less expensive than other feedstock materials, more widely available than other feedstock materials, or both.

According to embodiments described herein, it has been found that conventional hydrotreatment and/or hydrocracking processes may be improved by only subjecting portions of a feedstock oil to hydrocracking. In one or more embodiments, product selectivity, efficiency, or both may be improved by a method where a feedstock oil is hydrotreated (which may remove one or more of metals, sulfur, nitrogen) and, following hydrotreatment, is separated into at least a heavy fraction and a light, where the heavy fraction is subjected to hydrocracking and the light fraction is sent to a downstream refining process such as steam cracking.

According to one or more embodiments presently described, a feedstock oil may be processed by a method which may include one or more of hydrotreating the feedstock oil to reduce or remove one or more of sulfur content, metals content, nitrogen content, or aromatics content to produce a hydrotreated oil stream; separating at least a portion of the hydrotreated oil stream into a at least a lesser boiling point oil fraction stream and a greater boiling point oil fraction stream in a first separator; hydrocracking the greater boiling point oil fraction stream; and steam cracking the lesser boiling point oil fraction stream.

According to another embodiment, a feedstock oil may be processed by a method which may include one or more of hydrotreating the feedstock oil to reduce or remove one or more of sulfur content, metals content, nitrogen content, or aromatics content to produce a hydrotreated oil stream; separating the hydrotreated oil stream into at least a liquid hydrotreated oil stream and a gas hydrotreated oil stream in a first separator; separating the liquid hydrotreated oil stream into at least a lesser boiling point oil fraction stream and a greater boiling point oil fraction stream in a second separator; hydrocracking the greater boiling point oil fraction stream to from a hydrocracked effluent stream; passing the hydrocracked effluent stream to the first separator; and steam cracking the lesser boiling point oil fraction stream.

According to yet another embodiment, a feedstock oil may be processed by a method which may include one or more of hydrotreating the feedstock oil to reduce or remove one or more of sulfur content, metals content, nitrogen content, or aromatics content to produce a hydrotreated oil stream; separating the hydrotreated oil stream into at least a liquid hydrotreated oil stream and a gas hydrotreated oil stream in a first separator; separating the liquid hydrotreated oil stream into at least a lesser boiling point oil fraction stream and a greater boiling point oil fraction stream in a second separator; hydrocracking the greater boiling point oil fraction stream to from a hydrocracked effluent stream; separating the hydrocracked effluent stream into a least a gas hydrocracked recycle stream and a liquid hydrocracked recycle stream; and steam cracking the liquid hydrocracked recycle stream.

Additional features and advantages of the technology described in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
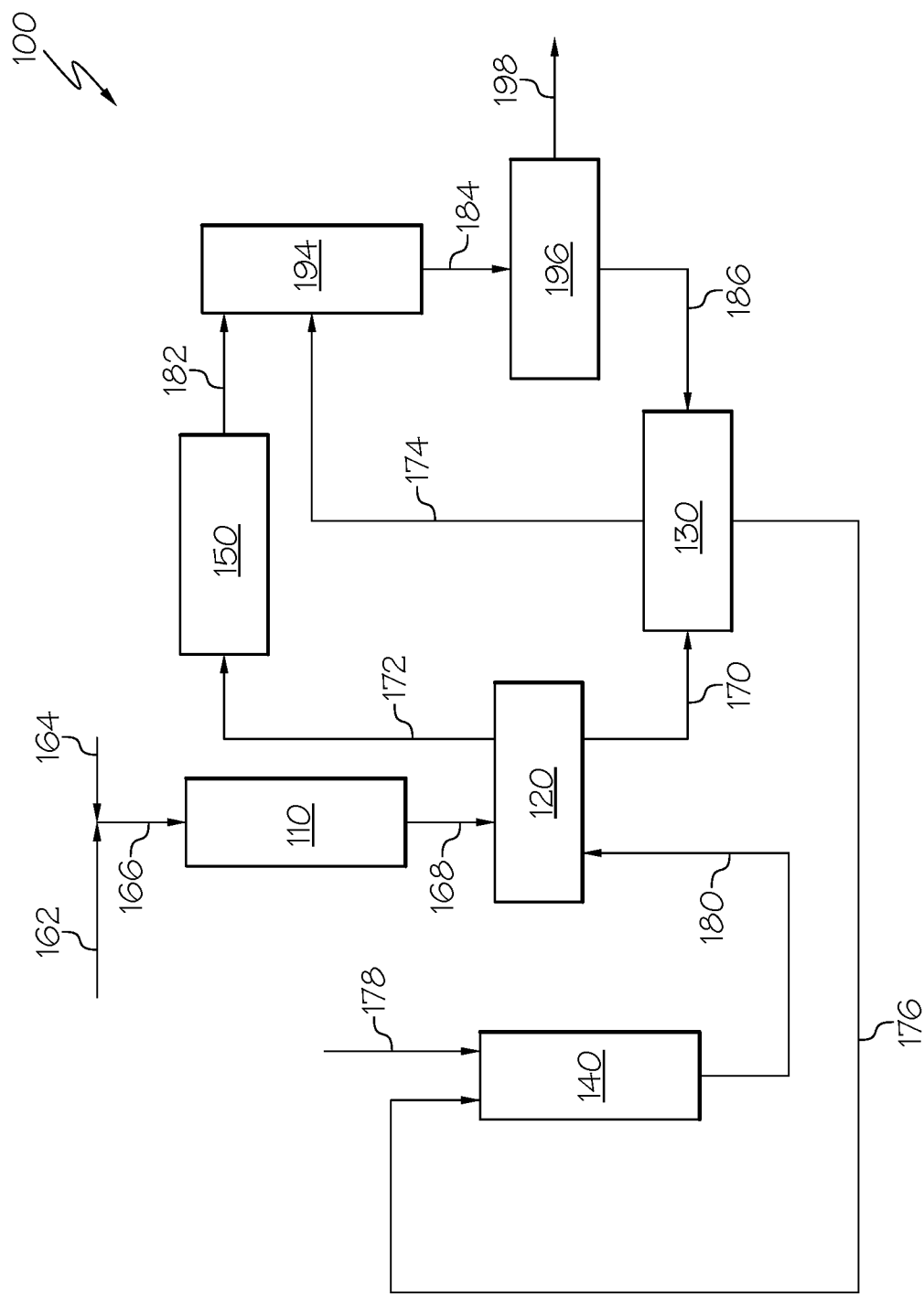
FIG. 1 depicts a generalized schematic diagram of an embodiment of a crude oil conversion system, according to one or more embodiments described in this disclosure.
Figure 2:
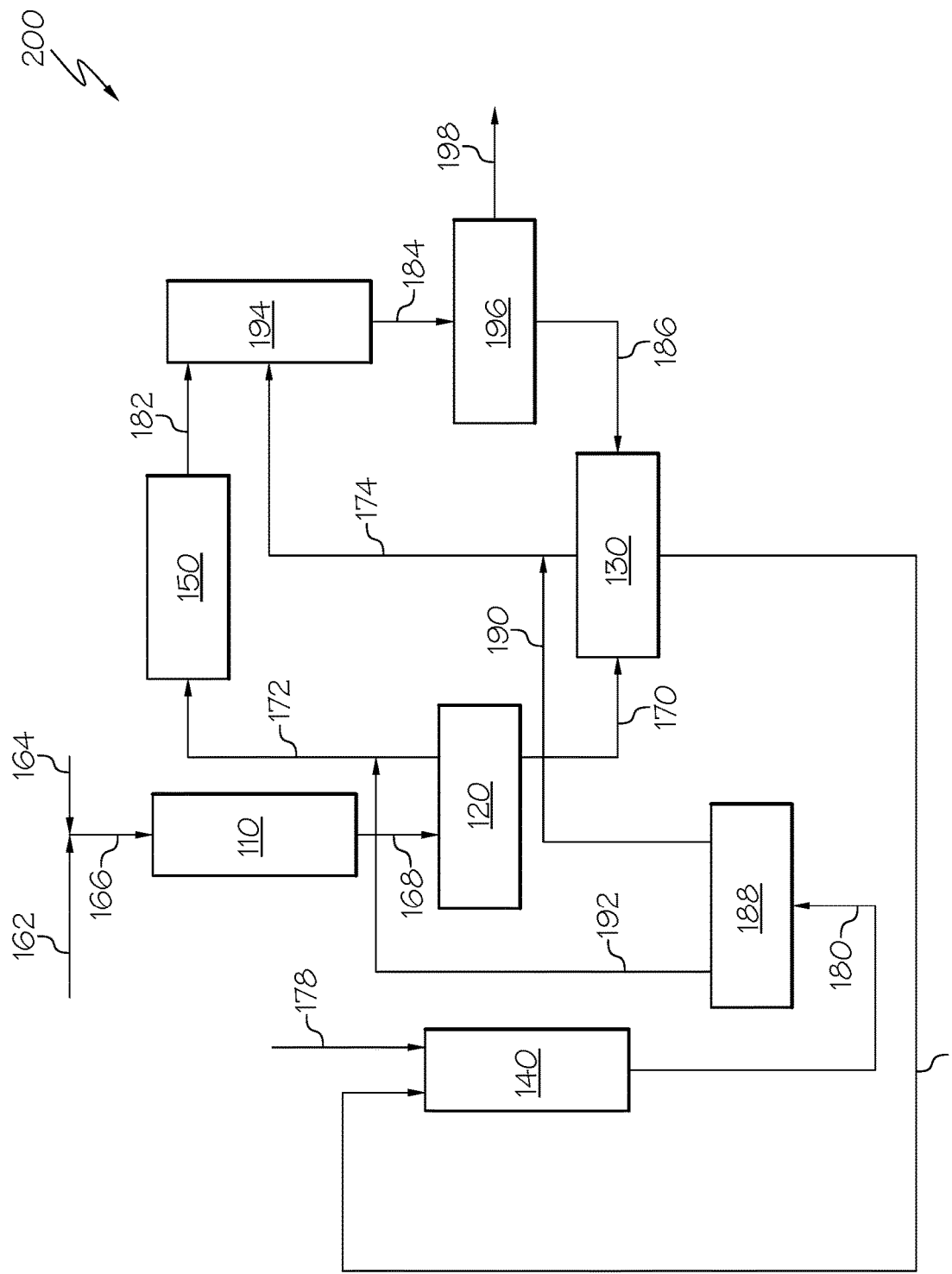
FIG. 2 depicts a generalized schematic diagram of another embodiment of a crude oil conversion system, according to one or more embodiments described in this disclosure.

For the purpose of describing the simplified schematic illustrations and descriptions of FIGS. 1 and 2, the numerous valves, temperature sensors, electronic controllers and the like that may be employed and well known to those of ordinary skill in the art of certain chemical processing operations are not included. Further, accompanying components that are often included in conventional chemical processing operations, such as refineries, such as, for example, air supplies, catalyst hoppers, and flue gas handling are not depicted. It should be understood that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines which may serve to transfer process steams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows which do not connect two or more system components signify a product stream which exits the depicted system or a system inlet stream which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a system product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagrams of FIGS. 1 and 2. Mixing or combining may also include mixing by directly introducing both streams into a like reactor, separation device, or other system component. For example, it should be understood that when two streams are depicted as being combined directly prior to entering a separation unit or reactor, that in some embodiments the streams could equivalently be introduced into the separation unit or reactor and be mixed in the reactor.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Described in this disclosure are various embodiments of systems and methods for processing heavy oil feedstocks, such as crude oil, into petrochemical products such as BTX and light olefins. According to one or more embodiments, the processing of the feedstock oil may include hydrotreating the feedstock oil to reduce or remove one or more of sulfur, metals, nitrogen and aromatics content, separating the hydrotreated crude oil into a liquid hydrotreated crude oil stream and a gas hydrotreated crude oil stream, separating the liquid hydrotreated crude oil stream into a lesser boiling point oil fraction stream and a greater boiling point oil fraction stream, hydrocracking the greater boiling point oil fraction stream, and steam cracking the lesser boiling point oil fraction stream. The products of the steam cracking reaction may be further separated into desired petrochemical product streams. For example, crude oil may be utilized as a feedstock oil and be directly processed into one or more of light olefins or BTX.

As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors such as fixed bed reactors, and fluidized bed reactors. One or more "reaction zones" may be disposed in a reactor. As used in this disclosure, a "reaction zone" refers to an area where a particular reaction takes place in a reactor. For example, a packed bed reactor with multiple catalyst beds may have multiple reaction zones, where each reaction zone is defined by the area of each catalyst bed.

As used in this disclosure, a "separation unit" refers to any separation device that at least partially separates one or more chemicals that are mixed in a process stream from one another. For example, a separation unit may selectively separate differing chemical species from one another, forming one or more chemical fractions. Examples of separation units include, without limitation, distillation columns, flash drums, knock-out drums, knock-out pots, centrifuges, filtration devices, traps, scrubbers, expansion devices, membranes, solvent extraction devices, and the like. It should be understood that separation processes described in this disclosure may not completely separate all of one chemical consistent from all of another chemical constituent. It should be understood that the separation processes described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided, or separated, into two or more process streams of desired composition. Further, in some separation processes, a "lesser boiling point fraction" (sometimes referred to as a "light fraction") and a "greater boiling point fraction" (sometimes referred to as a "heavy fraction") may exit the separation unit, where, on average, the contents of the lesser boiling point fraction stream have a lesser boiling point than the greater boiling point fraction stream. Other streams may fall between the lesser boiling point fraction and the greater boiling point fraction, such as an "intermediate boiling point fraction" stream.

It should be understood that an "effluent" generally refers to a stream that exits a system component such as a separation unit, a reactor, or reaction zone, following a particular reaction or separation, and generally has a different composition (at least proportionally) than the stream that entered the separation unit, reactor, or reaction zone.

As used in this disclosure, a "catalyst" refers to any substance which increases the rate of a specific chemical reaction. Catalysts described in this disclosure may be utilized to promote various reactions, such as, but not limited to, cracking (including aromatic cracking), demetalization, desulfurization, and denitrogenation. As used in this disclosure, "cracking" may generally refer to a chemical reaction where a molecule having carbon to carbon bonds is broken into more than one molecule by the breaking of one or more of the carbon to carbon bonds, or is converted from a compound which includes a cyclic moiety, such as an aromatic, to a compound which does not include a cyclic moiety or contains fewer cyclic moieties than prior to cracking, or where an aromatic compound becomes saturated.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "hydrogen stream" passing from a first system component to a second system component should be understood to equivalently disclose "hydrogen" passing from a first system component to a second system component.

Now referring to FIG. 1, an oil conversion system 100 is schematically depicted. The oil conversion system 100 may receive a feedstock oil stream 162 and directly processes the feedstock oil stream 162 to form one or more petrochemical product streams. While the present description and examples may specify crude oil as the material of the feedstock oil stream 162, it should be understood that the oil conversion systems 100 and 200 described with respect to the embodiments of FIGS. 1 and 2, respectively, are applicable for the conversion of a wide variety of feedstock oils (in feedstock oil stream 162), including, but not limited to, crude oil, vacuum residue, tar sands, bitumen, atmospheric residue, and vacuum gas oils. If the feedstock oil is crude oil, it may have an American Petroleum Institute (API) gravity of at least 22 degrees, such as from 22 degrees to 40 degrees, or from 22 degrees to 50 degrees. For example, the feedstock oil utilized may be an Arab light crude oil. Example properties for one particular grade of Arab heavy crude oil are shown in Table 1. It should be understood that, as used in this disclosure, a "feedstock oil" may refer to a raw oil which has not been previously processed (such as crude oil) or may refer to an oil which has undergone some degree of processing prior to being introduced to the oil conversion system 100 in the feedstock oil stream 162.

TABLE 1

Example of Arab Light Export Feedstock

| | |
|---|---|
| Density, g/ml (20° C.) | 0.8595 |
| API | 33.13 |
| C, wt. % | 85.29 |
| H, wt. % | 12.68 |
| S, wppm | 19400 |
| N, wppm | 849 |
| Asphaltenes, wt. % | 1.2 |
| Micro carbon residue, wt. % | 3.4 |
| V, ppm | 15 |
| Ni, ppm | 12 |
| As, ppm | 0.04 |
| Hg, ppm | <2 |
| Boiling Point Properties | |
| Initial Boiling Point/5 wt. % | 33° C./92° C. |
| 10 wt. %/20 wt. % | 133° C./192° C. |
| 30 wt. %/40 wt. % | 251° C./310° C. |
| 50 wt. %/60 wt. % | 369° C./432° C. |
| 70 wt. %/80 wt. % | 503° C./592° C. |
| 90 wt. %/95 wt. % | >720° C./>720° C. |
| End Boiling Point | >720° C. |

TABLE 1-continued

Example of Arab Light Export Feedstock

| Narrow fraction yield, wt. % | |
|---|---|
| C5-180° C. | 18 wt. % |
| 180-350° C. | 28.8 wt. % |
| 350-540° C. | 27.4 wt. % |
| >540° C. | 25.8 wt. % |

According to some embodiments, it may be desirable to utilize a feedstock oil that has a density that is less than 0.86 g/ml. In additional embodiments, the end point of the feedstock oil may be less than or equal to 720° C. In additional embodiments, the nitrogen content in the feedstock oil may be less than 900 parts per million by weight.

Still referring to FIG. 1, the feedstock oil stream 162 may be combined with a hydrogen stream 164 to form a mixed stream 166. The hydrogen stream 164 may be supplied from a source outside of the system, or may be supplied from a system recycle stream from hydrogen produced or recovered at some other location in the system. In another embodiment, the hydrogen stream 164 may be from a combination of sources such as partially being supplied from a raw hydrogen stream and partially supplied from a recycled hydrogen stream.

The mixed stream 166 may then be introduced to a hydrotreating unit 110. The hydrotreating unit 110 may at least partially reduce the content of one or more of metals, nitrogen, sulfur, and aromatic moieties. For example, the hydrotreated effluent stream 168 which exits the hydrotreating unit 110 may have reduced content of one or more of metals, nitrogen, sulfur, and aromatic moieties by at least 2%, at least 5%, at least 10%, at least 25%, at least 50%, or even at least 75%. For example, a hydrodemetalization (HDM) catalyst may remove a portion of one or more metals from a process stream, a hydrodenitrogenation (HDN) catalyst may remove a portion of the nitrogen present in a process stream, and a hydrodesulfurization (HDS) catalyst may remove a portion of the sulfur present in a process stream. Additionally, a hydrodearomatization (HDA) catalyst may reduce the amount of aromatic moieties in a process stream by cracking those aromatic moieties. It should be understood that a particular catalyst is not necessarily limited in functionality to the removal or cracking of a particular chemical constituent or moiety when it is referred to as having a particular functionality. For example, a catalyst identified in this disclosure as an HDN catalyst may additionally provide HDA functionality, HDS functionality, or both.

According to one or more embodiments, the hydrotreating unit 110 may include multiple catalysts arranged in multiple beds arranged, for example, in series. For example, the hydrotreating unit 110 may comprise one or more of a hydrocracking catalyst, a hydrodemetalization (HDM) catalyst, a hydrodesulfurization (HDS) catalyst, and a HDS/HDN catalyst, arranged in series. As described herein, a "HDS/HDN" catalyst may be functional to remove sulfur and nitrogen from the feedstock oil. The catalysts of the hydrotreating unit 110 may comprise one or more IUPAC Group 6, Group 9, or Group 10 metal catalysts such as, but not limited to, molybdenum, nickel, cobalt, and tungsten, supported on a porous alumina and/or zeolite support. For example, one or more of the catalysts of the hydrotreating unit 110 may comprise nickel and molybdenum on alumina, or cobalt and molybdenum on alumina. As used in this disclosure, the hydrotreating unit 110 serves to at least partially reduce the content of one or more of metals, nitrogen, sulfur, and aromatic moieties in the mixed stream 166, and should not be limited by the materials utilized as catalysts in the hydrotreating unit 110. According to one embodiment, one or more catalysts utilized to reduce sulfur, nitrogen, and/or metals content may be positioned upstream of a catalyst which is utilized to hydrogenate or crack aromatics in the reactant stream. According to one or more embodiments, the hydrotreating unit 110 may operate at a temperature of from 350° C. to 450° C. and at a pressure of from 130 bars to 160 bars. The hydrotreating unit 110 may operate with a liquid hour space velocity of from 0.1/hour to 1/hour. The volumetric hydrogen to oil ratio may be from 800 to 1200. According to one or more embodiments, the one or more catalysts of the hydrotreating unit 110 may not include zeolites.

According to one or more embodiments, the hydrotreating unit 110 may comprise an HDM catalyst, a transition catalyst, and an HDS/HDN catalyst in series. The HDM catalyst may be upstream of the transition catalyst, and the transition catalyst may be upstream of the HDS/HDN catalyst. The HDM catalyst, transition catalyst, and HDS/HDN catalyst, may be positioned in series, either contained in a single reactor, such as a packed bed reactor with multiple beds, or contained in two or more reactors arranged in series.

According to one or more embodiments, the HDM catalyst may comprise one or more metals from the International Union of Pure and Applied Chemistry (IUPAC) Groups 5, 6, or 8-10 of the periodic table. For example, the HDM catalyst may comprise molybdenum. The HDM catalyst may further comprise a support material, and the metal may be disposed on the support material. In one or more embodiments, the HDM catalyst may comprise a molybdenum metal catalyst on an alumina support (sometimes referred to as "Mo/$Al_2O_3$ catalyst"). It should be understood throughout this disclosure that metals that are contained in any of the disclosed catalysts may be present as sulfides or oxides, or even other compounds.

In additional embodiments, the HDM catalyst may include a metal sulfide on a support material, where the metal is selected from the group consisting of IUPAC Groups 5, 6, and 8-10 elements of the periodic table, and combinations thereof. The support material may be gamma-alumina or silica/alumina extrudates, spheres, cylinders, beads, pellets, and combinations thereof.

In one or more embodiments, the HDM catalyst may comprise a gamma-alumina support, with a surface area of from 100 $m^2/g$ to 160 $m^2/g$ (such as, from 100 $m^2/g$ to 130 $m^2/g$, or from 130 $m^2/g$ to 160 $m^2/g$). In some embodiments, the HDM catalyst may be described as having a relatively large pore volume, such as at least 0.8 $cm^3/g$ (for example, at least 0.9 $cm^3/g$, or even at least 1.0 $cm^3/g$). The pore size of the HDM catalyst may be predominantly macroporous (that is, having a pore size of greater than 50 nm). This may provide a large capacity for the uptake of metals on the HDM catalyst's surface and optionally dopants. In one embodiment, a dopant can be selected from the group consisting of boron, silicon, halogens, phosphorus, and combinations thereof.

In one or more embodiments, the HDM catalyst may comprise from 0.5 wt. % to 12 wt. % of an oxide or sulfide of molybdenum (such as from 2 wt. % to 10 wt. % or from 3 wt. % to 7 wt. % of an oxide or sulfide of molybdenum), and from 88 wt. % to 99.5 wt. % of alumina (such as from 90 wt. % to 98 wt. % or from 93 wt. % to 97 wt. % of alumina).

In one or more embodiments, the transition catalyst may comprise one metal from IUPAC Group 6 and one metal from IUPAC Groups 8-10. Example IUPAC Group 6 metals include molybdenum and tungsten. Example IUPAC Group 8-10 metals include nickel and cobalt. For example, the transition catalyst may comprise Mo and Ni on a alumina support (sometimes referred to as "Mo—Ni/$Al_2O_3$ catalyst"). The transition catalyst may also contain a dopant that is selected from the group consisting of boron, phosphorus, halogens, silicon, and combinations thereof. The transition catalyst can have a surface area of 140 $m^2/g$ to 200 $m^2/g$ (such as from 140 $m^2/g$ to 170 $m^2/g$ or from 170 $m^2/g$ to 200 $m^2/g$). The transition catalyst can have an intermediate pore volume of from 0.5 $cm^3/g$ to 0.7 $cm^3/g$ (such as 0.6 $cm^3/g$). The transition catalyst may, in some embodiments, comprise a mesoporous structure having pore sizes in the range of 12 nm to 50 nm. These characteristics may provide a balanced activity in HDM and HDS.

In one or more embodiments, the transition catalyst may comprise from 10 wt. % to 18 wt. % of an oxide or sulfide of molybdenum (such as from 11 wt. % to 17 wt. % or from 12 wt. % to 16 wt. % of an oxide or sulfide of molybdenum), from 1 wt. % to 7 wt. % of an oxide or sulfide of nickel (such as from 2 wt. % to 6 wt. % or from 3 wt. % to 5 wt. % of an oxide or sulfide of nickel), and from 75 wt. % to 89 wt. % of alumina (such as from 77 wt. % to 87 wt. % or from 79 wt. % to 85 wt. % of alumina).

In one embodiment, the HDS/HDN catalyst may include a metal oxide or sulfide on a support material, where the metal is selected from the group consisting of IUPAC Groups 5, 6, and 8-10 of the periodic table, and combinations thereof. The support material may include gamma-alumina, meso-porous alumina, silica, or both, in the form of extrudates, spheres, cylinders, pellets, or combinations thereof.

According to one or more embodiments, the HDS/HDN catalyst may comprise a gamma alumina based support that has a surface area of 180 $m^2/g$ to 240 $m^2/g$ (such as from 180 $m^2/g$ to 210 $m^2/g$, or from 210 $m^2/g$ to 240 $m^2/g$). This relatively large surface area for the HDS/HDN catalyst may allow for a smaller pore volume (for example, less than 1.0 $cm^3/g$, less than 0.95 $cm^3/g$, or even less than 0.9 $cm^3/g$). In one embodiment, the HDS/HDN catalyst may include at least one metal from IUPAC Group 6, such as molybdenum and at least one metal from IUPAC Groups 8-10, such as nickel. The HDS/HDN catalyst may also include at least one dopant selected from the group consisting of boron, phosphorus, silicon, halogens, and combinations thereof. In one embodiment, cobalt can be used to increase desulfurization of the HDS/HDN catalyst. In some embodiments, the HDS/HDN catalyst may have a higher metals loading for the active phase as compared to the HDM catalyst. This increased metals loading may cause increased catalytic activity. In one or more embodiments, the HDS/HDN catalyst comprises nickel and molybdenum, and has a nickel to molybdenum mole ratio (Ni/(Ni+Mo)) of 0.1 to 0.3 (such as from 0.1 to 0.2 or from 0.2 to 0.3). In an embodiment that includes cobalt, the mole ratio of (Co+Ni)/Mo may be in the range of 0.25 to 0.85 (such as from 0.25 to 0.5 or from 0.5 to 0.85).

According to one or more embodiments, the contents of the stream entering the hydrotreating unit 110 may have a relatively large amount of one or more of metals (for example, Vanadium, Nickel, or both), sulfur, or nitrogen. For example, the contents of the stream entering the hydroprocessing unit may comprise one or more of greater than 17 parts per million by weight of metals, greater than 135 parts per million by weight of sulfur, or greater than 50 parts per million by weight of nitrogen. The contents of the stream exiting the hydrotreating unit 110 may have a relatively small amount of one or more of metals (for example, Vanadium, Nickel, or both), sulfur, and nitrogen. For example, the contents of the stream exiting the hydrotreating unit 110 may comprise one or more of 17 parts per million by weight of metals or less, 135 parts per million by weight of sulfur or less, or 50 parts per million by weight of nitrogen or less.

The hydrotreated effluent stream 168, which may include hydrotreated oil, may exit the hydrotreating unit 110 and be passed to a high-low pressure separator 120. The high-low pressure separator 120 may separate the hydrotreated effluent stream 168 into gas components and liquid components. The gas components may exit the high-low pressure separator 120 as the gas hydrotreated oil stream 172 and the liquid components may exit the high-low pressure separator 120 as the liquid hydrotreated oil stream 170. According to one or more embodiments, the high-low pressure separator 120 may have a pressure which is similar to that of the hydrotreating unit 110, such as, for example, from 130 bars to 160 bars. The temperature of the high-low pressure separator 120 may be from 100° C. to 200° C. The temperature may be adjusted by passing the hydrotreated effluent stream through one or more heat exchangers. The gas hydrotreated oil stream may comprise one or more of hydrogen, $NH_3$, $H_2S$, or C1-C4 hydrocarbons.

Still referring to FIG. 1, the liquid hydrotreated oil stream 170 may be introduced to a separator 130 which separates the contents of the liquid hydrotreated oil stream 170 into a lesser boiling point oil fraction stream 174 and a greater boiling point oil fraction stream 176. In one or more embodiments, separator 130 may be a vapor-liquid separator such as a flash drum (sometimes referred to as a breakpot, knock-out drum, knock-out pot, compressor suction drum, or compressor inlet drum). In such an embodiment utilizing a vapor-liquid separator as the separator 130, the lesser boiling point oil fraction stream 174 exits the separator 130 as a vapor and the greater boiling point oil fraction stream 176 exits the separator 130 as a liquid. The vapor-liquid separator may be operated at a temperature and pressure suitable to separate the liquid hydrotreated oil stream 170 into the lesser boiling point oil fraction stream 174 and the greater boiling point oil fraction stream 176. A fractionating temperature may be defined as the approximate temperature where the contents of the lesser boiling point oil fraction have a boiling point less than the fractionating temperature and the contents of the greater boiling point oil fraction have a boiling point greater than the fractionating temperature. According to various embodiments, the fractionating temperature may be in the ranges of from 180° C. to 250° C., from 250° C. to 300° C., from 300° C. to 350° C., from 350° C. to 400° C., from 400° C. to 450° C., from 450° C. to 500° C., or from 500° C. to 540° C. For example, the contents of the lesser boiling point fraction may have boiling points of less than or equal to 180° C., 250° C., 300° C., 350° C., 400° C., 450° C., 500° C., or 540° C., and the contents of the greater boiling point fraction may have boiling points of greater than or equal to 180° C., 250° C., 300° C., 350° C., 400° C., 450° C., 500° C., or 540° C.

Following the separation of the liquid hydrotreated oil stream 170 into the lesser boiling point oil fraction stream 174 and the greater boiling point oil fraction stream 176, the lesser boiling point oil fraction stream 174 may be passed to a steam cracker unit 194. Additionally, the gas hydrotreated oil stream 172 may be passed to a gas plant 150, where it may be processed and valuable fuels, such as hydrogen, may be removed from the stream. The contents of the gas hydrotreated oil stream 172 following processing in the gas plant 150 may be passed in the gas plant effluent stream 182 to the steam cracker unit 194. The gas plant effluent stream 182 may include C2-C4 hydrocarbons. Alternatively, the gas plant effluent stream may exit the system and not enter the steam cracker unit 194.

The steam cracker unit 194 may include a convection zone and a pyrolysis zone. The lesser boiling point oil fraction stream 174 and the gas plant effluent stream 182 may pass into the convection zone along with steam. In the convection zone, the lesser boiling point oil fraction stream 174 and the gas plant effluent stream 182 may be pre-heated to a desired temperature, such as from 400° C. to 650° C. The contents of the lesser boiling point oil fraction stream 174 and gas plant effluent stream 182 present in the convection zone may then be passed to the pyrolysis zone where they are steam-cracked. According to one or more embodiments, the pyrolysis zone may operate at a temperature of from 700° C. to 900° C. The pyrolysis zone may operate with a residence time of from 0.05 seconds to 2 seconds. The mass ratio of steam to lesser boiling point oil fraction stream 174 may be from about 0.3:1 to about 2:1. Additional cooling, such as by heat exchanger, may be performed on the steam cracked contents to form a steam-cracked effluent stream 184. The steam-cracked effluent stream 184 may include a mixture of cracked hydrocarbon-based materials. For example, steam-cracked effluent stream 184 may include one or more of pyrolysis oil, gasoline, mixed butenes, hydrogen, methane, butane, butene, propane, propene, ethylene, ethane, benzene, toluene, or xylene. It is noted that, in one or more embodiments, additives such as $NH_3$ or organic nitrogen may not be needed to be introduced to the system since the post treatment cracking is by steam cracking.

The steam-cracked effluent stream 184 may be passed to one or more separation units 196 where it may be separated into one or more system product streams 198. For example, the separation units 196 may be one or more distillation columns which separates the contents of steam-cracked effluent stream 184 into one or more streams that include ethylene, propene, butene, benzene, toluene, xylene, or combinations thereof. The system product streams 198 may contain petrochemical products sometimes used as intermediates in downstream chemical processing. The separation unit 196 may also separate 180° C.-500° C. pyrolysis oil from the BTX and light olefin product streams 198. The pyrolysis oil may exit the separation unit 196 in the pyrolysis oil recycle stream 186, which is passed to the separator 130, where it subsequently is separated into the greater boiling point oil fraction stream 176 and the lesser boiling point oil fraction stream 174.

Referring again to the greater boiling point oil fraction stream 176 exiting the separator 130, the greater boiling point oil fraction stream 176 may be passed to a hydrocracking unit 140. The hydrocracking unit 140 may be a packed bed reactor, and may comprise a hydrocracking catalyst. In one or more embodiments, the hydrocracking catalyst may comprise zeolite (such as zeolite Beta or zeolite Y), one or more metal oxide support materials, and one or more metal catalysts. The hydrocracking catalyst may have a material composition comprising from 10 wt. % to 80 wt. % of one or more metal oxide support materials (for example, alumina), from 18 wt. % to 32 wt. % of metal catalyst material, and from 10 wt. % to 60 wt. % of the zeolite. The metal catalyst material may comprise one or more metals from IUPAC Groups 5, 6, 8, 9, or 10 of the periodic table. For example, the hydrocracking catalyst may comprise one or more metals from IUPAC Groups 5 or 6, and one or more metals from IUPAC Groups 8, 9, or 10 of the periodic table. For example, the hydrocracking catalyst may comprise molybdenum or tungsten from IUPAC Group 6 and nickel or cobalt from IUPAC Groups 8, 9, or 10. In one embodiment, the hydrocracking catalyst may comprise tungsten and nickel metal catalyst. In another embodiment, the hydrocracking catalyst may comprise molybdenum and nickel metal catalyst. In another embodiment, the hydrocracking catalyst may comprise platinum and palladium metal catalyst. For example, in one embodiment, the hydrocracking catalyst may comprise from 20 wt. % to 26 wt. % of a sulfide or oxide of tungsten, from 4 wt. % to 6 wt. % of an oxide or sulfide of nickel, from 10 wt. % to 70 wt. % of a metal oxide support material such as alumina, and from 10 wt. % to 60 wt. % of zeolite. In another embodiment, the hydrocracking catalyst may comprise from 14 wt. % to 16 wt. % of an oxide or sulfide of molybdenum, from 4 wt. % to 6 wt. % of an oxide or sulfide of nickel, from 20 wt. % to 80 wt. % of a metal oxide support material such as alumina, and from 10 wt. % to 60 wt. % of zeolite. Without being bound by theory, it is believed that the reduction or removal of nitrogen, sulfur, metals, or combinations thereof, such as in the hydrotreating unit, may help to avoid poisoning the hydrocracking catalyst.

According to one or more embodiments, hydrogen 178 may be introduced along with the greater boiling point oil fraction stream 176 into the hydrocracking unit 140. The hydrocracking unit 140 may operate at a temperature of, for example, from 300° C. to 440° C. and at a pressure of, for example, from 130 bars to 160 bars. The hydrocracking unit 140 may operate with a liquid hour space velocity of from 0.2/hour to 1/hour. The volumetric hydrogen to oil ratio may be from 800 to 1500.

The hydrocracked components of the greater boiling point oil fraction stream 176 following processing by the hydrocracking unit 140 may exit the hydrocracking unit 140 in a hydrocracked effluent stream 180. The hydrocracked effluent stream 180 may have reduced amount of aromatic content as compared to the greater boiling point oil fraction stream 176. For example, aromatic content in the hydrocracked effluent stream 180 may be reduced by at least 10%, at least 20%, at least 30%, at least 40%, at least 50%, at least 60%, at least 70%, at least 80%, or even at least 90%.

The hydrocracked effluent stream 180 may be passed to the high-low pressure separator 120. Once introduced to the high-low pressure separator 120, the contents of the hydrocracked effluent stream 180 are separated into the liquid hydrotreated oil stream 170 and the gas hydrotreated oil stream 172.

Now referring to FIG. 2, an oil conversion system 200 is depicted which in some aspects is similar or identical to oil conversion system 100, but where the hydrocracked effluent stream 180 is passed to a second high-low pressure separator 188. Similar in operation to the high-low pressure separator 120, the second high-low pressure separator 188 may separate the hydrocracked effluent stream 180 into gas components and liquid components. The gas components may exit the second high-low pressure separator 188 as the gas hydrocracked recycle stream 192 and the liquid components exit the second high-low pressure separator 188 as the liquid hydrocracked recycle stream 190. The gas hydrocracked recycle stream 192 may be combined with the gas hydrotreated oil stream 172 and subsequently be introduced to the gas plant 150. The liquid hydrocracked recycle stream 190 may be combined with the lesser boiling point oil fraction stream 174 and subsequently be introduced to the steam cracker unit 194 for processing. The configuration of FIG. 2 may be particularly well suited for the processing of lighter crude oils, such as Arab extra light crude oil. These oils may, for example, have API gravities of at least 35 degrees, or even at least 37 degrees. Crude oils with this range of API gravity may be sufficiently light such that the portion which is hydrocracked can enter the steam cracker unit 194 without further processing.

Examples

The various embodiments of methods and systems for the conversion of a feedstock oils will be further clarified by the following examples. The examples are illustrative in nature, and should not be understood to limit the subject matter of the present disclosure.

An Arab light crude oil was used as a feedstock (the properties of which are shown in Table 2), which was hydrotreated with a series of catalyst beds of KFR-22 catalyst, KFR-33 catalyst, and KFR-70 catalyst, respectively (each commercially available from Albemarle Corporation of Charlotte, N.C.). Tables 3A and 3B provide details regarding the operating conditions of the hydrotreating process and the resulting effluent streams for hydrotreatment conditions A-E where liquid hourly space velocity (LHSV) and temperature were varied (while pressure was constant at 150 bar for Conditions A-E).

TABLE 2

| Feedstock Oil Properties | |
|---|---|
| Density | 0.8607 |
| C, wt % | 85.58 |
| H, wt % | 12.37 |
| S, ppmw | 19810 |
| N, ppmw | 733 |
| Ni, ppm | 4 |
| V, ppm | 15 |
| SimDis, ° C. | |
| IBP | 29.4 |
| 5% | 77.2 |
| 10% | 112.2 |
| 20% | 178.9 |
| 30% | 237.2 |
| 40% | 292.8 |
| 50% | 344.4 |
| 60% | 401.1 |
| 70% | 460.6 |
| 80% | 529.4 |
| 90% | 613.9 |
| 95% | 672.8 |
| EBP | 739.4 |
| Narrow fraction yield, wt. % | |
| <180° C. | 20.2 |
| 180-350° C. | 30.8 |
| 350-540° C. | 30.3 |
| >540° C. | 18.8 |

TABLE 3A

| Sample Name | Condition A | Condition B | Condition C | Condition D | Condition E |
|---|---|---|---|---|---|
| Operation conditions | | | | | |
| LHSV, h$^{-1}$ | 0.2 | 0.2 | 0.3 | 0.3 | 0.5 |
| Temperature, ° C. | 390 | 400 | 390 | 400 | 390 |
| Product yields, wt. % | | | | | |
| Chemical H$_2$ consumption | 1.92 | 1.94 | 1.53 | 2.01 | 1.27 |
| H$_2$S | 2.06 | 2.06 | 2.05 | 2.05 | 2.00 |
| NH$_3$ | 0.10 | 0.10 | 0.08 | 0.09 | 0.05 |
| C1 | 0.35 | 0.50 | 0.27 | 0.48 | 0.21 |

TABLE 3A-continued

| Sample Name | Condition A | Condition B | Condition C | Condition D | Condition E |
|---|---|---|---|---|---|
| C2-C4 | 0.88 | 0.37 | 0.28 | 0.30 | 0.05 |
| C5-180° C. | 19.97 | 19.93 | 17.84 | 20.32 | 15.25 |
| 180-350° C. | 44.16 | 44.59 | 38.15 | 43.26 | 38.08 |
| 350-540° C. | 27.35 | 27.68 | 29.50 | 28.81 | 30.43 |
| >540° C. | 7.18 | 6.60 | 13.06 | 6.60 | 15.15 |
| C5+ liquid yield | 98.66 | 98.81 | 98.55 | 98.99 | 98.90 |

TABLE 3B

| Sample Name | Condition A | Condition B | Condition C | Condition D | Condition E |
|---|---|---|---|---|---|
| Operation conditions | | | | | |
| LHSV, h$^{-1}$ | 0.2 | 0.2 | 0.3 | 0.3 | 0.5 |
| Temperature, ° C. | 390 | 400 | 390 | 400 | 390 |
| Density, g/ml | 0.8244 | 0.8255 | 0.8375 | 0.8255 | 0.8509 |
| C, wt % | 85.57 | 85.70 | 86.04 | 85.63 | 86.09 |
| H, wt % | 14.43 | 14.30 | 13.93 | 14.37 | 13.80 |
| S, wppm | 1.8 | 8.6 | 126.5 | 17.47 | 638.7 |
| N, wppm | <5 | 10.3 | 178.5 | 23.2 | 407.7 |
| Asphaltenes, wt % | <0.5 | <0.5 | <0.5 | <0.5 | <0.5 |
| V, ppm | <1 | <1 | <1 | <1 | <1 |
| Ni, ppm | <1 | <1 | <1 | <1 | 1.67 |
| SimDis, ° C. | | | | | |
| IBP | 70 | 72 | 69 | 70 | 73 |
| 5% | 113 | 113 | 112 | 110 | 124 |
| 10% | 139 | 139 | 140 | 136 | 154 |
| 20% | 179 | 179 | 189 | 178 | 202 |
| 30% | 216 | 216 | 232 | 217 | 247 |
| 40% | 252 | 252 | 275 | 254 | 289 |
| 50% | 289 | 289 | 317 | 292 | 331 |
| 60% | 327 | 326 | 366 | 331 | 379 |
| 70% | 373 | 371 | 420 | 377 | 432 |
| 80% | 428 | 424 | 483 | 426 | 497 |
| 90% | 506 | 500 | 567 | 500 | 588 |
| 95% | 568 | 560 | 619 | 560 | 655 |
| EBP | 679 | 673 | 700 | 672 | 703 |

To simulate hydrocracking a heavy fraction of the hydrotreated oil, the 180° C.+ boiling point portion of the hydrotreated Arab light crude was hydrocracked with a hydrocracking catalysts made of CBV-760 zeolite (commercially available from Zeolyst International of Malvern, Pa.), MoO$_3$ and NiO, and gamma alumina. The results of the hydrocracking of the heavy fraction are summarized in Table 4. The zeolite contents in Catalyst Sample X and Catalyst Sample Y are 50 wt. % and 30 wt. %, respectively. Each of Catalyst Sample X and Y contained 15 wt. % MoO$_3$ and 5 wt. % NiO, with the remainder being gamma alumina. The results are shown for LHSV=0.8 and 390° C., 150 bar H$_2$ pressure. It is noted that with Catalyst Sample X, almost all 540° C.+ fraction was converted.

TABLE 4

| 2$^{nd}$ stage HCK catalyst | Catalyst Sample X | Catalyst Sample Y |
|---|---|---|
| Product properties | | |
| Density | 0.771 | 0.7988 |
| S, ppmw | 230 | 287.0 |
| N, ppmw | <5 | 3.0 |
| Product yield, wt. % | | |
| C1 | 0.4 | 0.39 |
| C2 | 0.6 | 0.48 |
| C3 | 2.1 | 1.15 |
| nC4 | 3.8 | 1.34 |
| iC4 | 2.7 | 1.38 |
| <180° C. | 40.3 | 20.0 |
| 180-350° C. | 34.7 | 47.6 |
| 350-540° C. | 13.2 | 23.2 |
| >540° C. | 0.0 | 4.8 |

The steam cracking results with the system of FIG. 1 were modeled using Aspen HYSYS based on the experimental hydrotreating and hydrocracking tests explained herein, along with results from a system similar to that of FIG. 1 but without the two-stage hydrotreating and hydrocracking of a heavy fraction. Instead, this comparative example utilized the hydrocracking catalyst immediately after the hydrotreating step and did not separate a heavy fraction for hydrocracking. As shown in Table 5, olefin yields were greater in the FIG. 1 embodiment.

TABLE 5

| System | No separate hydrocracking of heavy fraction | FIG. 1 embodiment |
|---|---|---|
| Conditions | | |
| HC-flow, g/h | 3600 | 3600 |
| H2O-flow, g/h | 3600 | 3600 |
| COT, ° C. | 840 | 840 |
| COP, bar abs | 1.8 | 1.8 |
| Yields, wt % | | |
| ΣC4– | 52.4 | 59 |
| P/E | 0.4 | 0.5 |
| C/H (ΣC4–) | 4.2 | 4.7 |
| C/H (C5-C10) | 9.1 | 10.2 |
| C/H (C10+) | 10.6 | 12 |
| Total Olefin, wt. % | 40.3 | 45.6 |
| H2 | 0.6 | 0.7 |
| CH4 | 10.2 | 11.3 |
| C2H6 | 2.7 | 2.7 |
| C2H4 | 20.7 | 23.2 |
| C3H8 | 0.4 | 0.4 |
| C3H6 | 10.3 | 11.6 |
| n-C4H10 | 0.1 | 0.1 |
| i-C4H10 | 0.0 | 0 |
| Propadiene (PD) | 0.3 | 0.3 |
| C2H2 | 0.4 | 0.4 |
| t-2-C4H8 | 0.3 | 0.4 |
| 1-C4H8 | 1.1 | 1.1 |
| i-C4H8 | 1.2 | 1.4 |
| c-2-C4H8 | 0.3 | 0.3 |
| 1,3-C4H6 | 3.7 | 4.6 |
| Methylacetylene (MeAc) | 0.3 | 0.4 |
| C5+ | | |
| Benzene | 4.7 | 5.7 |
| Toluene | 3.8 | 5.0 |
| Xylenes | 1.2 | 2.5 |
| C5-C10 (excel. BTX) | 8.4 | 8.5 |
| C10+ | 18.1 | 19.1 |
| Coke formation | | |
| Reactor (g coke/hr) | 0.6 | 0.4 |

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A method for processing a feedstock oil, the method comprising:
    hydrotreating the feedstock oil to reduce or remove one or more of sulfur content, metals content, nitrogen content, or aromatics content to produce a hydrotreated oil stream;
    separating at least a portion of the hydrotreated oil stream into only a lesser boiling point oil fraction stream and a greater boiling point oil fraction stream in a flash drum;
    hydrocracking the greater boiling point oil fraction stream; and
    steam cracking the lesser boiling point oil fraction stream.

2. The method of claim 1, wherein the feedstock oil is crude oil.

3. The method of claim 2, wherein the crude oil has an American Petroleum Institute (API) gravity of from 22 degrees to 40 degrees.

4. The method of claim 1, wherein a hydrocracked effluent stream is formed by the hydrocracking of the greater boiling point oil fraction stream, and wherein the hydrocracked effluent stream is recycled to the hydrotreated oil stream.

5. The method of claim 1, wherein the steam cracking of at least the lesser boiling point oil fraction forms a steam-cracked effluent stream comprising one or more of pyrolysis oil, gasoline, mixed butenes, hydrogen, methane, butane, butene, propane, propene, ethylene, ethane, benzene, toluene, or xylene.

6. The method of claim 1, wherein the steam cracking of at least the lesser boiling point oil fraction forms a steam-cracked effluent stream, and wherein the steam-cracked effluent stream is separated into one or more system product streams and a pyrolysis oil stream.

7. The method of claim 6, wherein the pyrolysis oil stream is passed to the first separator.

8. The method of claim 1, wherein the feedstock oil is hydrotreated in a hydrotreating unit comprising two or more catalysts in series.

9. A method for processing a feedstock oil, the method comprising:
    hydrotreating the feedstock oil to reduce or remove one or more of sulfur content, metals content, nitrogen content, or aromatics content to produce a hydrotreated oil stream;
    separating the hydrotreated oil stream into at least a liquid hydrotreated oil stream and a gas hydrotreated oil stream in a first separator;
    separating the liquid hydrotreated oil stream into only a lesser boiling point oil fraction stream and a greater boiling point oil fraction stream in a flash drum;
    hydrocracking the greater boiling point oil fraction stream to from a hydrocracked effluent stream;
    passing the hydrocracked effluent stream to the first separator; and
    steam cracking the lesser boiling point oil fraction stream.

10. The method of claim 9, wherein the gas hydrotreated oil stream is processed in a gas plant to form a gas plant effluent stream.

11. The method of claim 10, wherein the gas plant effluent stream is steam cracked.

12. The method of claim 9, wherein the steam cracking of at least the lesser boiling point oil fraction forms a steam-cracked effluent stream comprising one or more of pyrolysis oil, gasoline, mixed butenes, hydrogen, methane, butane, butene, propane, propene, ethylene, ethane, benzene, toluene, or xylene.

13. The method of claim 9, wherein the steam cracking of at least the lesser boiling point oil fraction forms a steam-cracked effluent stream, and wherein the steam-cracked effluent stream is separated into one or more system product streams and a pyrolysis oil stream.

14. The method of claim 13, wherein the pyrolysis oil stream is passed to the second separator.

15. The method of claim 9, wherein the feedstock oil is crude oil.

16. A method for processing a feedstock oil, the method comprising:

hydrotreating the feedstock oil to reduce or remove one or more of sulfur content, metals content, nitrogen content, or aromatics content to produce a hydrotreated oil stream;

separating the hydrotreated oil stream into at least a liquid hydrotreated oil stream and a gas hydrotreated oil stream in a first separator;

separating the liquid hydrotreated oil stream into only a lesser boiling point oil fraction stream and a greater boiling point oil fraction stream in a flash drum;

hydrocracking the greater boiling point oil fraction stream to from a hydrocracked effluent stream;

separating the hydrocracked effluent stream into at least a gas hydrocracked stream and a liquid hydrocracked stream; and steam cracking the liquid hydrocracked stream.

17. The method of claim 16, further comprising combining the gas hydrocracked stream with the gas hydrotreated oil stream.

18. The method of claim 16, further comprising combining the liquid hydrocracked stream with the lesser boiling point oil fraction stream.

19. The method of claim 16, wherein the feedstock oil is crude oil.

* * * * *